(12) United States Patent
Adoni

(10) Patent No.: US 9,907,938 B2
(45) Date of Patent: Mar. 6, 2018

(54) PLASTER WITH MEDICATION DISPENSER

(71) Applicant: AID-TEC, Ramat Gan (IL)

(72) Inventor: Sharon Adoni, Closter, NJ (US)

( * ) Notice: Subject to any disclaimer, the term of this patent is extended or adjusted under 35 U.S.C. 154(b) by 211 days.

(21) Appl. No.: 14/188,324

(22) Filed: Feb. 24, 2014

(65) Prior Publication Data

US 2015/0238740 A1    Aug. 27, 2015

(51) Int. Cl.
*A61M 35/00* (2006.01)
*A61F 13/00* (2006.01)
*A61M 37/00* (2006.01)
*A61F 11/00* (2006.01)

(52) U.S. Cl.
CPC ....... *A61M 35/00* (2013.01); *A61F 13/00063* (2013.01); *A61F 2013/00553* (2013.01)

(58) Field of Classification Search
CPC ....... A61M 35/00; A61M 37/00; A61F 13/00; A61F 11/00
See application file for complete search history.

(56) References Cited

U.S. PATENT DOCUMENTS

| | | |
|---|---|---|
| 2,595,606 A | 5/1952 | Pohjola |
| 7,067,709 B2 | 6/2006 | Murata et al. |
| 2008/0167633 A1 | 7/2008 | Vannucci |
| 2012/0022474 A1 | 1/2012 | Adoni et al. |

FOREIGN PATENT DOCUMENTS

| | | |
|---|---|---|
| WO | 2000074616 A1 | 12/2000 |
| WO | 2009128075 A1 | 10/2009 |

*Primary Examiner* — Tatyana Zalukaeva
*Assistant Examiner* — Ilya Treyger

(57) ABSTRACT

An adhesive wound plaster includes a substrate having an adhesive layer on one major surface thereof on which is located a pad that is adapted to be placed directly over a wound and held on the skin by the substrate's adhesive. The plaster further incorporates a capsule having a dispensing neck at least partially overlaying the pad and where the capsule contains a medicament. When the capsule is squeezed, a rupturable seal on the neck breaks and the medicament is made to coat the pad prior to applying the plaster to the skin such that the pad overlays the wound. A piece of removable release paper covers at least a portion of the adhesive layer prior to use.

9 Claims, 2 Drawing Sheets

PLASTER WITH MEDICATION DISPENSER

CROSS REFERENCE TO RELATED APPLICATIONS

None

BACKGROUND OF THE INVENTION

I. Field of the Invention

The present invention relates generally to wound covering plasters, and more particularly to wound covering plasters incorporating a built-in dispenser for applying a fluid medicament to a pad forming a component part of the plaster.

II. Discussion of the Prior Art

In my earlier published U.S. Application 2012/0022474 A1, there is disclosed a plaster with a built-in medication dispenser in which there is an adhesive strip adapted to adhere the plaster to a person's skin in covering relation to a wound. Affixed to the adhesive strip is a pair of pads that are in a stacked relation to one another. Also affixed to the adhesive strip is a dome-shaped capsule containing a medicament, the capsule having a tubular conduit portion forming a neck and with a rupturable seal at an end of the neck. By depressing or squeezing the dome-shaped capsule, the increase in fluid pressure ruptures the seal, allowing the medicament to flow into the interface between the stacked pair of pads. That published application also teaches having the adhesive layer, pads and capsule overlaid with a removable protective covering strip that is to be peeled off from the adhesive strip of the plaster just prior to applying the medicament to the pad interface and the plaster to a wound.

It has been found that certain medicaments do not readily permeate through the pad that contacts the skin when the plaster is applied over a wound and thus the wound and surrounding skin does not receive the benefit of the medicament. I have redesigned my earlier plaster construction to overcome this drawback.

SUMMARY OF THE INVENTION

In accordance with the present invention, there is provided a wound plaster comprising a base layer of a flexible material of a predetermined shape and size with first and second major surfaces. A layer of pressure sensitive, medical grade, non-allergenic adhesive is applied to the second major surface and a single wound-contacting pad is adhered to the strip by the adhesive layer. Also located and releasably retained on the base layer is a somewhat rigid yet thin card on which a compressible capsule containing a medicament is formed. The capsule includes a channel or neck portion leading onto the pad. The neck portion includes a rupturable seal. Squeezing the capsule increases the hydraulic pressure within the capsule sufficient to rupture the seal and allow a flow of the medicament onto the surface of the wound contacting pad. Completing the wound plaster is a removable protective layer comprising a release paper of material that is adhered to a second portion of the strip by the adhesive layer, the protective layer covering the exposed adhesive on the adhesive strip and the wound contacting pad. This removable protective layer will be peeled free from the adhesive layer and the capsule squeezed followed by removal of the card with the now-compressed empty capsule from the adhesive strip at a time of application of the plaster to a wound.

DESCRIPTION OF THE DRAWINGS

The foregoing features, objects and advantages of the invention will become apparent to those skilled in the art from the following detailed description of a preferred embodiment, especially when considered in conjunction with the accompanying drawings in which like numerals in the several views refer to corresponding parts.

DESCRIPTION OF THE PREFERRED EMBODIMENTS

Figure 1:
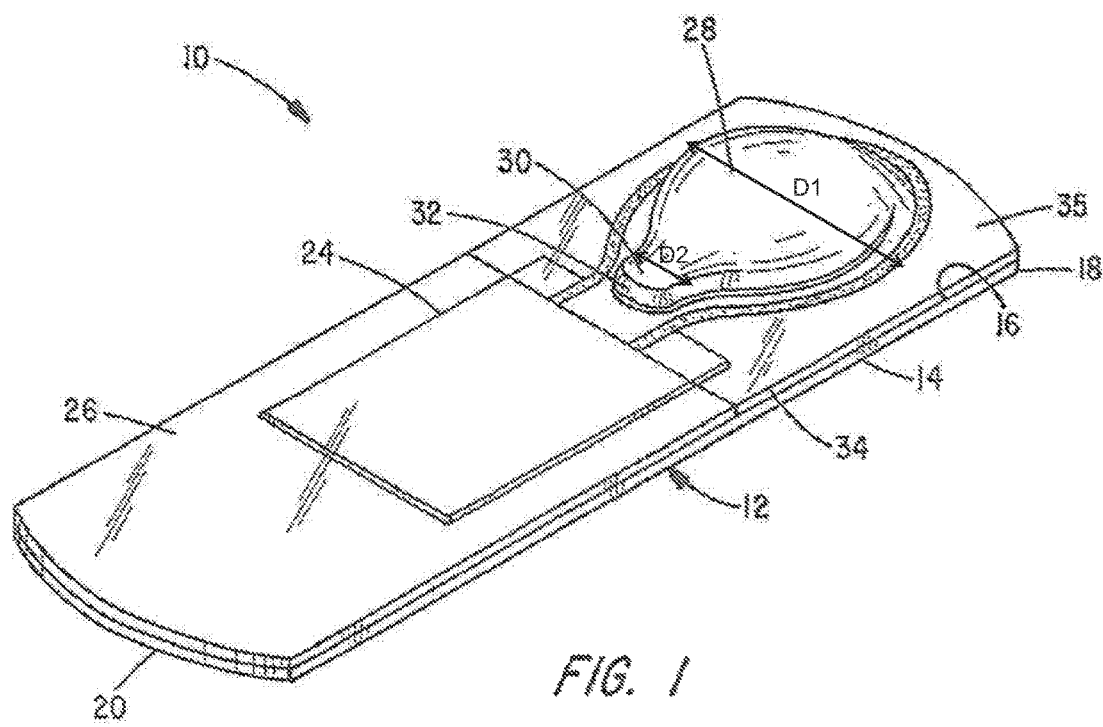
FIG. 1 is a top perspective view of a preferred embodiment of the present invention.
Figure 2:
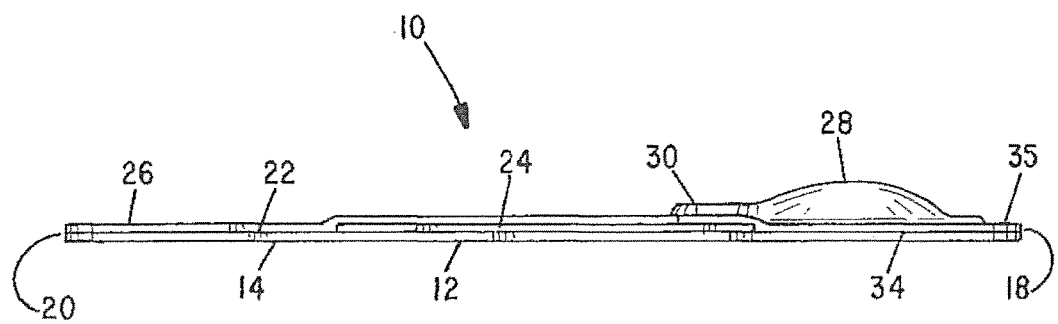
FIG. 2 is a side elevation view.

This description of the preferred embodiments is intended to be read in connection with the accompanying drawings, which are to be considered part of the entire written description of this invention. In the description, relative terms such as "lower", "upper", "horizontal", "vertical", "above", "below", "up", "down", "top" and "bottom" as well as derivatives thereof (e.g., "horizontally", "downwardly", "upwardly", etc.) should be construed to refer to the orientation as then described or as shown in the drawings under discussion. These relative terms are for convenience of description and do not require that the apparatus be constructed or operated in a particular orientation. Terms such as "connected", "connecting", "attached", "attaching", "join" and "joining" are used interchangeably and refer to one structure or surface being secured to another structure or surface or integrally fabricated in one piece, unless expressively described otherwise.

Figure 3:
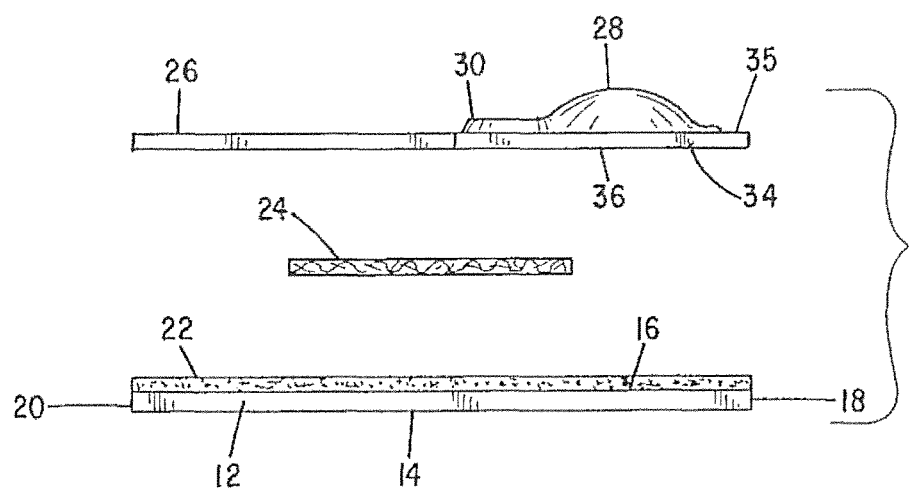
FIG. 3 is an exploded view thereof.

Referring first to FIG. 1, a plaster, constructed in accordance with the present invention, is identified generally by numeral 10. It is seen to include an outer base layer 12 comprising a flexible substrate of a plastic or fabric material of a type commonly used on adhesive bandages and having a first major surface 14, a second major surface 16 and first and second ends 18 and 20. As seen in FIG. 3, the second major surface 16 is coated with a layer 22 of a pressure sensitive, medical grade, hypoallergenic adhesive 22 on its entire surface. Adhered to the adhesive layer 22 is a pad 24 of gauze or other suitable material. Shown extending from end 20 and releasably affixed to the adhesive 22 and overlaying the pad 24 is a protective, removable covering layer 26 that conforms to the shape of the base layer 12. It is made of a release paper material that readily allows it to be peeled free from the adhesive layer 22 while leaving the adhesive intact.

Also removably adhered to the adhesive layer 22 is a relatively rigid yet thin card 34 overlaid by a plastic layer 35 that forms a dome-shaped capsule 28 that projects upward from the card 34. The dome has an integrally formed neck portion 30 leading from a frangible seal 32 on the capsule 28 that is designed to rupture. More particularly, the capsule 28 is filled with a fluid medicament, such as a liquid, cream or gel. Neck portion 30 is oriented parallel with the card 34 and connects the dome-shaped capsule on one end and the frangible seal on an opposite end. The neck portion having a width D2 less than half a diameter D1 of the dome-shaped capsule. By pinching or squeezing the dome-shaped capsule 28 against the underlying card 34, the hydraulic pressure applied to the seal 32 results in its rupture and resulting application of the capsule contents directly onto the pad 24. The card 34 covers and protects the adhesive layer 22 that is not subtended by protective layer 26 and incorporates a release material layer 36 (FIG. 3) on its undersurface so that removal of the card and capsule does not impair the adhesive layer 22.

Prior to application of the wound plaster to a wound, the covering layer 26, along with the dome 28 and the card 34 on which it resides, both of which serve to protect the pad 24 and adhesive layer 22 from exposure to potentially harmful contamination, are removed. The protective covering layer 26 and the card 34 with its capsule 28 can be peeled free from the adhesive layer 22 in a way that does not materially decrease the tackiness of the adhesive layer and its ability to adhere to the skin of a person. Once removed, the resulting plaster 10 is then applied in covering relation to a wound. In this regard, the pad 24, now coated or containing the medicament, is applied directly over the wound with the remaining portion of the plaster 12 serving to adhesively affix the plaster to the surrounding skin.

Without limitation, the capsule may be made to contain a medicament that promotes coagulation of blood or which contains an antibiotic or antiseptic for promoting wound healing with reduced incidences of infection.

This invention has been described herein in considerable detail in order to comply with the patent statutes and to provide those skilled in the art with the information needed to apply the novel principles and to construct and use such specialized components as are required. However, it is to be understood that the invention can be carried out by specifically different equipment and devices, and be used with a variety of wounds caused by accident or surgery. For example, and without limitation, the flexible substrate 12 may not only be rectangular, as shown in the drawings, but may instead be square, circular or oval in a plan view and may be produced in a variety of sizes (e.g., small, medium, large) to accommodate a particular wound condition. It is further contemplated that rather than employing a protective covering layer like 26 in FIG. 1, it may be replaced by a second medicament dispenser, like dome 28 on card 34 where the card 34 on each are made to completely overlay the adhesive layer 22. Also, various modifications, both as to the equipment and operating procedures, can be accomplished without departing from the scope of the invention itself.

What is claimed is:

1. A wound plaster comprising:
   an elongate substrate of a flexible material with first and second end portions and first and second major surfaces, and with a layer of pressure sensitive medical grade adhesive on the second major surface;
   a single wound contacting pad centrally disposed between the first and second end portions and adhered to the substrate by the adhesive layer;
   a relatively rigid card member having a release material on its undersurface and a plastic layer on its upper surface, the plastic layer defining a dome-shaped capsule having a diameter and a neck portion having a length parallel with the elongate substrate and a width, the neck portion having the dome formed at one end and leading to a frangible seal formed at an opposite end and containing a medicament, the capsule protruding up from the card member and the card member being removably adhered to the adhesive on the substrate proximate one of the first and second end portions with the neck portion and frangible seal at least partially overlaying the wound contacting pad; and
   a removable protective layer of material adhered to the substrate by the adhesive layer and overlaying the other end portion's adhesive layer and the wound contacting pad;
   wherein the card member is positioned under the dome-shaped capsule, the width of the neck is less than half the diameter of the dome-shaped capsule and when pressure is applied to the dome-shaped capsule, the card member provides rigidity causing the frangible seal to rupture due to increased hydraulic pressure acting on the frangible seal and deposits the medicament directly on a top surface of the wound contacting pad prior to adhering the wound plaster to the wound.

2. The wound plaster as in claim 1 wherein the medicament is one of a liquid, cream and gel.

3. The wound plaster as in claim 1 where in the removable protective layer is peeled free from the adhesive layer at a time of application of the plaster to a wound.

4. The wound plaster of claim 1 wherein the card member with its capsule is adapted to be removable from the substrate prior to application of the wound plaster to a wound.

5. The wound plaster of claim 1 wherein the pad comprises a liquid absorbent material.

6. The wound plaster as in claim 1 wherein the substrate is of a shape, in a plan view, of one of a rectangle and an oval.

7. A wound plaster comprising:
   a) a layer of a flexible material of a predetermined shape having first and second major surfaces and with a layer adhesive on its second major surface;
   b) only a single wound contacting pad adhered to the flexible material by the layer of adhesive; and
   c) a layer of a flexible plastic disposed on a rigid card member defining a dome shaped capsule containing a fluid medicament, the capsule including an integrally formed neck leading to the wound contacting pad, the neck extending from a frangible seal on one end forming the capsule at a second end, said card member supporting the capsule and releasably adhered to the layer of adhesive in covering relation to at least one portion of the adhesive layer, the arrangement being such that compression of the capsule with a predetermined force is supported by the card member causing an increase in hydraulic pressure sufficient to rupture the frangible seal and release the medicament directly onto a surface of the wound contacting pad, prior to adhering the wound plaster to the wound.

8. The wound plaster of claim 7 and further including a flexible piece of release paper covering a portion of the adhesive layer not covered by said card member.

9. The wound plaster as in claim 7 and further including a second relatively rigid card member with a second layer of flexible plastic thereon defining a second dome-shaped capsule containing a fluid medicament releasably adhered to the layer of adhesive in covering relation to the adhesive layer other than in said at least one portion.

* * * * *